United States Patent [19]
Benjamin

[11] Patent Number: 4,885,288
[45] Date of Patent: Dec. 5, 1989

[54] PHARMACEUTICAL COMPOSITIONS CONTAINING LYSINE ACETYLSALICYLATE

[75] Inventor: Lennette Benjamin, New York, N.Y.

[73] Assignee: Synthelabo, Paris, France

[21] Appl. No.: 103,698

[22] Filed: Oct. 2, 1987

[30] Foreign Application Priority Data

Dec. 22, 1986 [FR] France ............... 86 17991

[51] Int. Cl.⁴ .......................................... A61K 31/615
[52] U.S. Cl. ..................................................... 514/162
[58] Field of Search ............................ 514/159, 162

[56] References Cited

PUBLICATIONS

Chem. Abst-93-125427w (1980), 101-482n (1984).
Osamo, N. et al., "Therapeutic Effect of Aspirin in Sickle Cell Anaemia", Acta Haemat. 66: 102-107 (1981).
Thompson, E. et al., "Pharmacological Actions of Diaspirins, Potential Antisickling Agents: Analgesic and Anti-Inflammatory Effects", Res-Commun-Chem-Pathol-Pharmacol, 1985, 48/3 (381-388).
Chatterjee, R. et al., "Structural Features Required for the Reactivity and Intracellular Transport of bis(3,5-dibromosalicyl)fumarate and Related Anti-Sickling Compounds, etc.", J-Biol-Chem, 1984, 259/23 (14863-14873).
Delaney, E. et al., "Alternative Di Aspirins for Modification of Hemoglobin and Sickle Hemoglobin", Arch-Biochem-Biophys 228 (2), 1984, 627-638.
Martin, J. et al., "Managing the Parturient with Sickle Cell Crisis", Clin-Obstet-Gynecol, 1984, 27/1 (39-49).
Massil, S. et al., "Acylation of Hemoglobin by Aspirin--Like Diacyl Esters", J. Pharm. Sci., 73(7), 1013-14.
Massil, S. et al., "Electrostatic Effects in Acylation of Hemoglobin by Aspirins", J. Pharm. Sci., 1984, 73/12 (1851-1853).
Zago, M. et al., "Treatment of Sickle Cell Diseases with Aspirin", Acta-Haematol, 1984, 72/1 (61-64).
Chang, H. et al., "Comparative Evaluation of Fifteen Anti-Sickling Agents", Blood 1983, Apr. vol. 61(4), 693-704.
Greenberg, J. et al., "Trial of Low Doses of Aspirin as Prophylaxis in Sickle Cell Disease", J. Pediatr., 1983 May, vol. 102 (5), pp. 781-784.
Balcerzak, S. et al., "Preliminary Studies of Continuous Extra-Corporeal Carbamylation in the Treatment of Sickle Cell Anemia", L-Lab-Clin-Med, 1982, 100/3 (345-355).
Bernstein, R. et al., "Some Pharmacologic Inhibitors of Complement Activity", Int-J-Immunopharmacol 4 (4), 1982, 381.
Cheng, L. et al., "Chemical Modification of Hemoglobin in Intact Whose Cells: Morphological Studies by Scanning Electron Microscope", Int. J. Biochem., 14(6), 461-5.
Osamo, N., "Aspirin in Sickle-Cell Anemia", Acta-Haematol, 1982, 68/4 (347).
Ozsoylu, S., "Aspirin in Sickle-Cell Anemia", Acta-Haematol-(Basel), 1982, vol. 68(4), p. 347.
Klotz, I. et al., "Rational Approaches to Chemotherapy: Anti-Sickling Agents", Science, 1981 Aug. 14, vol. 213 (4509, pp. 724-731).
Osamo, N. et al., "Therapeutic Effect of Aspirin in Sickle Cell Anemia", Acta-Haematol-(Basel), 1981, vol. 66(2), pp. 102-107.
Wood, L. et al., "Structural Specificities in Acylation of Hemoglobin and Sickle Hemoglobin by Diaspirins", J-Biol-Chem., 1981, 256/13 (7046-7052).
Chaplin, H. et al., "Aspirin-Dipyridamole Prophylaxis of Sickle Cell Disease Pain Crises", Thromb-Haemostasis, 1980, 43/3 (218-221).
Franklin, I. et al., "The Molecular Basis of Antisickling Agents", Trans-R-Soc-Trop-Med-Hyg, 1980, 74/6 (695-700).
Machlin, J. et al., "Effects of Aspirin and Related Drugs in Vitamin E Deficient Rats", J. Nutr., 110(10), 1958-64.
Zaugg, R. et al., "Modification of Hemoglobin with Analogs of Aspirin", J-Biol-Chem., 1980, 255/7 (2816-2821).
Alkjaersig, N. et al., "Experience with Aspirin-Dipyridamole Prophylaxis in Sickle Cell Disease", Thromb-Haemostasis, 1979, 42/1 (Nr. 0134).
Kokkini, G. et al., "The Design of New Antisickling Drugs", Inserm Symp., vol. date 1978, 9.
Arnow, P. et al., "Aspirin, Hyperventilation, and Cerebellar Infraction in Sickle Cell Disease", Arch-Intern-Med., 1978, Jan., vol. 138(1), pp. 148-149.
Machlin, L., "Vitamin E and Prostaglandins (PG)", Tocopherol, Oxygen Biomembr. Proc. Int. Symp., Meeting date 1977, 179-89.
Noguchi, C. et al., "Inhibition of Sickle Hemoglobin Gelation by Amino-Acids and Related Compounds", Biochemistry 17 (25), 1978, 5455-5459.
Protass, L., "Hyperventilation in Sickle Cell Disease", Arch-Intern-Med., 1978, 138/1 (29).
Walder, J. et al., "Alternative Aspirins as Anti-Sickling Agents Acetyl-345-Dibromo Salicylic Acid", Proc--Natl-Acad-Sci-U.S.A., 74 (12), 1977, 5499-5503.
Alkjaersig, N. et al., "Homostatic Alterations Accompanying Sickle Cell Pain Crises", JLABCLINMED, 1976, 83/3 (440-449).
Laasberg, L. et al., "Effect of Sodium P Amino Salicylate on Oxygen Affinity in Normal Sickle and Fetal (List continued on next page.)

Primary Examiner—Stanley J. Friedman
Attorney, Agent, or Firm—Fleit, Jacobson, Cohn, Price, Holman & Stern

[57] ABSTRACT

Pharmaceutical composition, useful for the treatment of drepanocytosis, which contains lysine acetylsalicylate.

1 Claim, No Drawings

OTHER PUBLICATIONS

Human Blood", J. Pharmacol Exp. Ther., 199 (2), 441–453 (1976).

Bridges, K. et al., "Acetylation of Hemoglobin by Aspirin", Proc. Natl., Symp. Sickle Cell Dis., 1st Meeting Date 1974, 185–6.

Laasberg, L. et al., "P Amino Salicylate Shifts the Dissociation Curve of Normal Sickle and Fetal Blood to the Right", Fed. Proc. 34 (3) 862.

Phadke, M. et al., "Hyperhaemolytic and Vascular Occlusive Crises in Sickle Cell Disease", J. Assoc. Phys. India, 1975, Jan., vol. 23 (1), pp. 41–44.

Hernandez, P., "New Aspects in the Treatment of Sickle Cell Anemia", REVCUBAPEDIAT, 1974, 46/2 (177–181).

Huntsman, R. et al., "Treatment of Sickle-Cell Disease", Br. J. Haematol, 1974, Dec., vol. 28(4), pp. 437–444.

Rabinowitz, Israel et al., "Light Scattering Studies of Retardation of Sickling by Aspirin-Like Drugs", Res. Commun. Chem. Pathol. Pharmacol., 8(2), 417–420.

Ritchey, J., "Sickle Cell Anemia, Effects of Acetylsalicylic Acid and of D-Glucose on Hemoglobin S", Diss. Abstr. Int. B, 1975, 35(10), 4810.

Shamsuddin, M. et al., "Sites of Acetylation of Sickle Cell Hemoglobin by Aspirin", Proc. Natl. Acad. Sci., U.S.A., 71(12), 1974, 4693–7.

Athreya, B. et al., "Aspirin-Induced Abnormalities of Liver Function", Am. J. Dis. Child., 1973, Nov., vol. 126 (5), pp. 638–641.

DeFuria, F. et al., "The Effect of Aspirin on Sickling and Oxygen Affinity of Erythrocytes", PROCNATACADSCI, U.S.A., 1973, 70/12(II), (3707–3710).

Klotz, I. et al., "Acetylation of Sickle Cell Hemoglobin by Aspirin", Proc. Nat. Acad. Sci., U.S.A., 70(5), 1313–15, 1973.

Mullick, F. et al., "Sickle Cell Crisis Associated with Drugs", Arch-Environ-Health, 1973, Apr., vol. 26 (4), pp. 221–222.

Alkjaersig, N., "Experience with Aspirin Dipyridamole Prophylaxis in Sickle Cell Disease", 7th Intl. Congress on Thrombosis and Haemostasis, Thromb Haemostasis 42(1), 1979, 60.

PHARMACEUTICAL COMPOSITIONS CONTAINING LYSINE ACETYLSALICYLATE

Pharmaceutical compositions containing lysine acetylsalicylate form the subject of the present invention.

While pursuing its investigation relating to lysine acetylsalicylate, the Applicant Company has observed that lysine acetylsalicylate, when administered by the intravenous route, is very active in the treatment of patients suffering from drepanocytosis.

The latter suffer from pain attacks which are different to treat. In these, several medicaments have proved inactive or insufficiently active for treating these pains. With its analgesic and antiinflammatory properties, lysine acetylsalicylate enables patients to be treated effectively.

Indeed, it is observed that after administering, by the intravenous route, several doses (4 to 5 doses on average) of lysine acetylsalicylate, each dose being equivalent to 500 mg of acetylsalicyclic acid, the patients' pains either disappeared or decreased to a large extent.

The treatment duration may vary depending on the patients and the pain intensity.

Indeed, in some patients, a decrease in pain intensity, a concomitant reduction in swellings and suppression of the "chest pain syndrome" can be observed from the time of administering intravenously the third or the fourth dose of lysine acetylsalicylate.

The pharmaceutical compositions of the invention contain lysine acetylsalicylate in a quantity corresponding to 500 mg or 1,000 mg of acetylsalicylic acid in combination with any suitable excipient, in particular any excipient suitable for administration by the intravenous route.

An example of pharmaceutical composition is as follows:

Lysine acetylsalicylate: 0.9 g, 1.8 g glycine: 0.1 g, 0.2 g which is dissolved extemporaneously in 5 ml water for injectable preparations.

I claim:

1. A process for the treatment of drepanocytosis comprising intravenously administering to a patient suffering from drepanocytosis a pharmaceutical composition comprising an effective amount of Lysine acetylsalicylate in combination with an intravenously administrable excipient, wherein said effective amount is effective for the amelioration of the symptoms of drepanocytosis.

* * * * *